United States Patent [19]

Irmer et al.

[11] Patent Number: 5,314,333
[45] Date of Patent: May 24, 1994

[54] DEVICE FOR GENERATING OSCILLATIONS FOR DENTAL APPLICATIONS

[75] Inventors: Joachim Irmer, Happenweiler Strasse 19, D-7997 Immenstaad; Detlef Kersting, Immenstaad, both of Fed. Rep. of Germany

[73] Assignee: Joachim Irmer, Immenstaad, Fed. Rep. of Germany

[21] Appl. No.: 959,255

[22] Filed: Oct. 9, 1992

[30] Foreign Application Priority Data

Oct. 18, 1991 [DE] Fed. Rep. of Germany ....... 4134428

[51] Int. Cl.⁵ ............................ A61C 1/02; A61C 1/07
[52] U.S. Cl. ...................................... 433/120; 433/98; 433/118; 433/119
[58] Field of Search ................. 433/118, 119, 98, 120, 433/123, 86

[56] References Cited

U.S. PATENT DOCUMENTS

| | | | |
|---|---|---|---|
| 3,106,021 | 10/1963 | Borden | 433/98 |
| 3,703,037 | 11/1972 | Robinson | 433/86 |
| 3,763,411 | 10/1973 | Goof | 433/119 |
| 3,822,801 | 8/1970 | Robinson | 433/86 |
| 4,428,748 | 1/1984 | Peyman et al. | 433/119 |
| 4,634,376 | 1/1987 | Mossle et al. | 433/118 |
| 4,634,420 | 1/1987 | Spinosa et al. | 433/119 |
| 4,797,098 | 1/1989 | Kawata | 433/98 |
| 4,804,364 | 2/1989 | Dieras et al. | 433/119 |
| 4,958,963 | 9/1990 | Perrault | 433/98 |
| 5,125,837 | 6/1992 | Warrin et al. | 433/86 |

*Primary Examiner*—Paul J. Hirsch
*Attorney, Agent, or Firm*—Robert W. Becker & Associates

[57] ABSTRACT

A device for generating oscillations for dental applications has an actuator connectable to an energy source and provided with a lifting member. The actuator is connected via a hydraulic linkage to the working device. Via the hydraulic linkage the oscillations generated by the actuator are transmitted onto a workpiece, for example, a crown. With this embodiment it is possible to transmit the mechanical oscillations generated by the actuator onto the crown so that the binder between the crown and the tooth stump is evenly distributed and compressed in a short period of time.

25 Claims, 7 Drawing Sheets

DEVICE FOR GENERATING OSCILLATIONS FOR DENTAL APPLICATIONS

BACKGROUND OF THE INVENTION

The present invention relates to a device which is especially suitable for generating oscillations for dental applications.

In dental practice, for the fixation of crowns, bridges or similar parts to tooth stumps, binders, for example in the form of cement or plastic material are used which, before application of the crown, are manually stirred or mechanically agitated and then filled into the crown or bridge. The distribution of the binder however is insufficient during the active cementing as well as during the passive application because the binder may not reach all the gaps and niches of the crown and/or of the tooth stump. Correspondingly, air bubbles may form, and furthermore, the binding time during which the patient must apply pressure with his jaws is relatively long.

It is therefore an object of the present invention to provide a device of the aforementioned kind with which it is possible to distribute evenly and/or compress the binder in a crown, a bridge or similar means to be positioned on a tooth stump before and after application of the crown between it and the tooth stump in a simple manner and in a short period of time with a corresponding device without endangering the patient even though work may have to be performed in the patient's mouth. The constructive expenditure should be minimal so that an economic manufacture of the device is possible. First of all, the device should provide for an easy handling, especially during insertion of bridges and crowns.

BRIEF DESCRIPTION OF THE DRAWINGS

This object, and other objects and advantages of the present invention, will appear more clearly from the following specification in conjunction with the accompanying drawings, in which.

SUMMARY OF THE INVENTION

Figure 1:
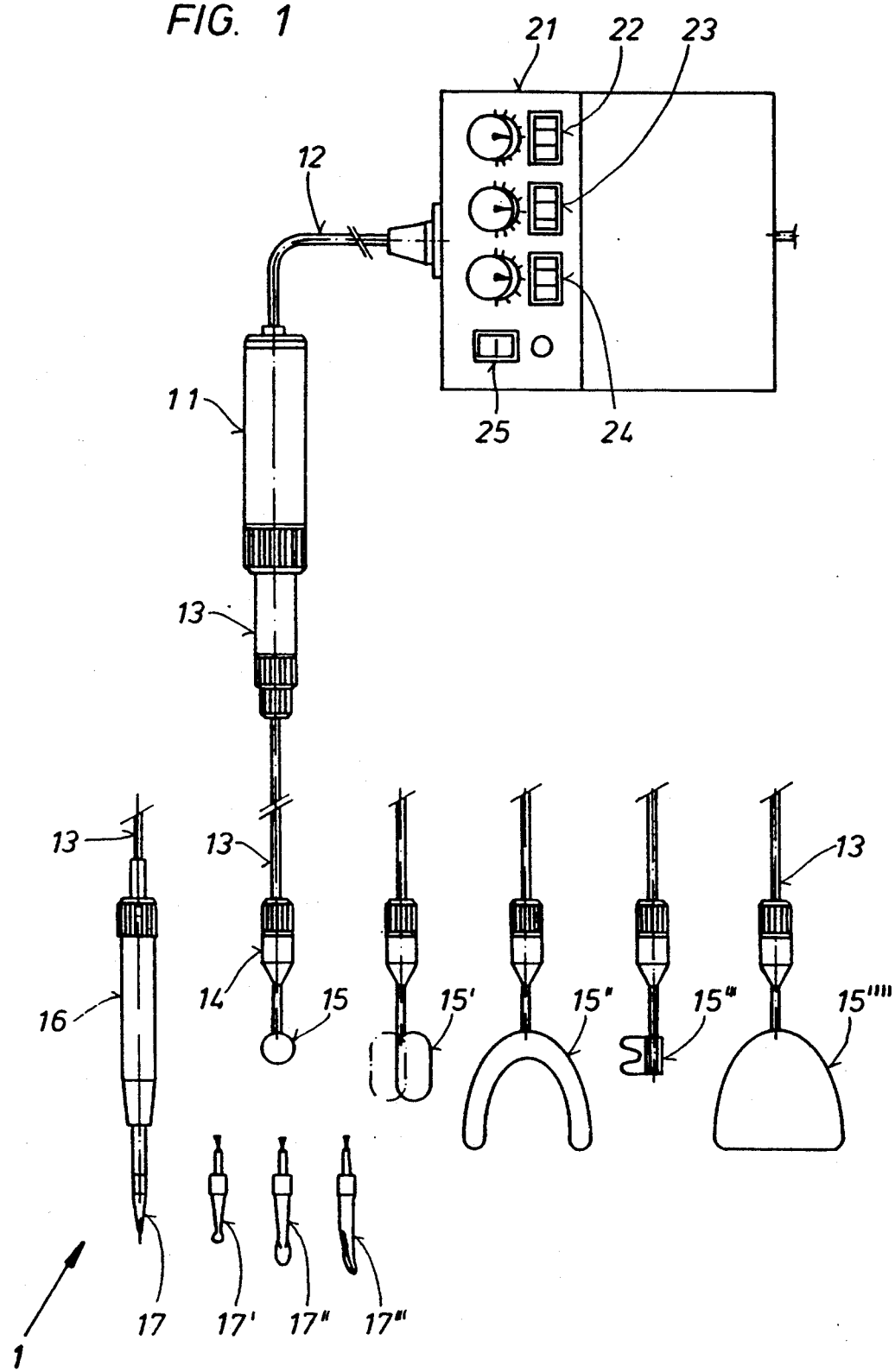
FIG. 1 is a device for generating oscillations together with a control device in a schematic representation; also shown are different actuators in the form of resonators and filling stamps.

The inventive device for generating oscillations for dental application is primarily characterized by:

an actuator for generating oscillations, the actuator connectable to an energy source and comprising a lifting member;

a hydraulic linkage with a first and a second end, the first end connected to the lifting member; and a working device, connected to the second end of the hydraulic linkage, for transmitting the oscillations of the actuator to a workpiece, for example, in the form of a crown, a bridge, a tooth filling etc.

The actuator may be in the form of a solenoid, especially a reversing lifting solenoid, an ultrasonic oscillator, a piezoelectric translator, or a rotation motor comprising a cam wheel, whereby the lifting member is a plunger that cooperates with the cam wheel.

It is advantageous that the actuator further comprises a control device for adjusting stroke, frequency, and lifting energy of the lifting member. Advantageously, the hydraulic linkage comprises a line connected between the lifting member and the working device, the line filled with an incompressible medium, and further comprising a cylinder and a piston at the first end, the piston inserted into the cylinder and actuatable by the lifting member. The incompressible medium may be, for example, a medicinal oil. The hydraulic linkage further comprises a diaphragm for closing the line at the second end. A further means for closing the line at the second end is a bellows.

Preferably, the line is at least partially comprised of a flexible hose and further comprises a first screw connection for connecting the hose to the cylinder. A second screw connection may be provided for connecting the hose to the working device. In another embodiment, the line comprises an intermediate piece and a third screw connection for connecting the hose to the intermediate piece. Preferably, the inventive device further comprises a compensating device for compensating a loss of the incompressible medium. The compensating device is preferably connected to the line in the area of the cylinder. Furthermore, it is advantageous to provide a pressure measuring device for measuring a pressure of the incompressible medium within the line, whereby the pressure measuring device is preferably connected to the line in the area of the cylinder.

Advantageously, the hydraulic linkage further comprises a first semi-spherical intermediate piece interposed between the piston and the lifting member. A second semi-spherical intermediate piece may be interposed between the diaphragm and the working device.

Expediently, the working device is a resonator and the diaphragm is inserted into the resonator. The resonator preferably has a grip portion. The diaphragm has connected thereto a pressure-transmitting piece in the form of a parallelepipedal biting cushion made of expanded virgin polytetrafluoroethylene.

The working device may also be in the form of a filling stamp having a grip portion. The diaphragm or the bellows may act directly or via the intermediate pieces onto the working device, i.e., the resonator or the filling stamp.

When a device for generating oscillations according to the present invention is embodied as an actuator provided with a lifting member that is connected via a hydraulic linkage to the working device, it is possible to transmit the generated mechanical oscillations from the actuator to the working device and thus to the workpiece, for example, a crown or a bridge. In this manner, it is reliably ensured that the binder is evenly distributed and compressed within the crown and between the crown and tooth stump before and after its positioning. The binder is forced into all of the gaps and niches of the crown and the tooth stump so that not only the fastening of the crown to the stump is improved, but also air bubbles are prevented and the curing time is shortened relative to the known methods.

Furthermore, the handling of the device is very simple since the mechanical oscillations generated by the actuator which are transmitted via the hydraulic linkage to the working device, are transmitted without difficulties to the workpiece. Since the patient is only exposed to a device which operates within a frequency range of approximately 40 to 100 Hz, the application of the inventively embodied device in dentistry and the treatment of patients is without any risk because no actively electrically operated components are introduced into the patient's mouth.

DESCRIPTION OF PREFERRED EMBODIMENTS

The present invention will now be described in detail with the aid of several specific embodiments utilizing FIGS. 1 through 9.

Figure 2:
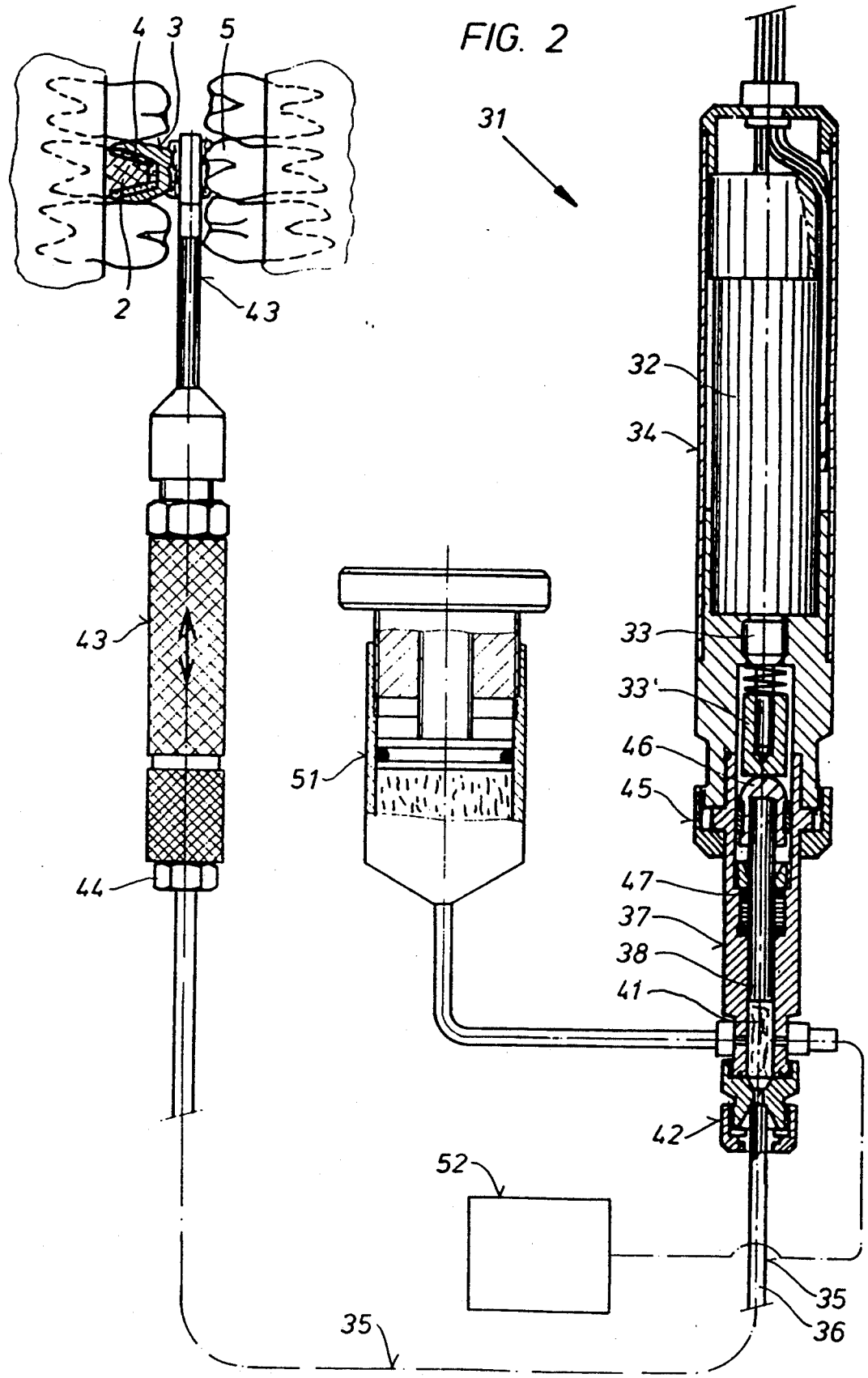
FIG. 2 shows an actuator in the form of an electric motor with a hydraulic linkage and resonators connected thereto in a partially sectioned view.
Figure 3:
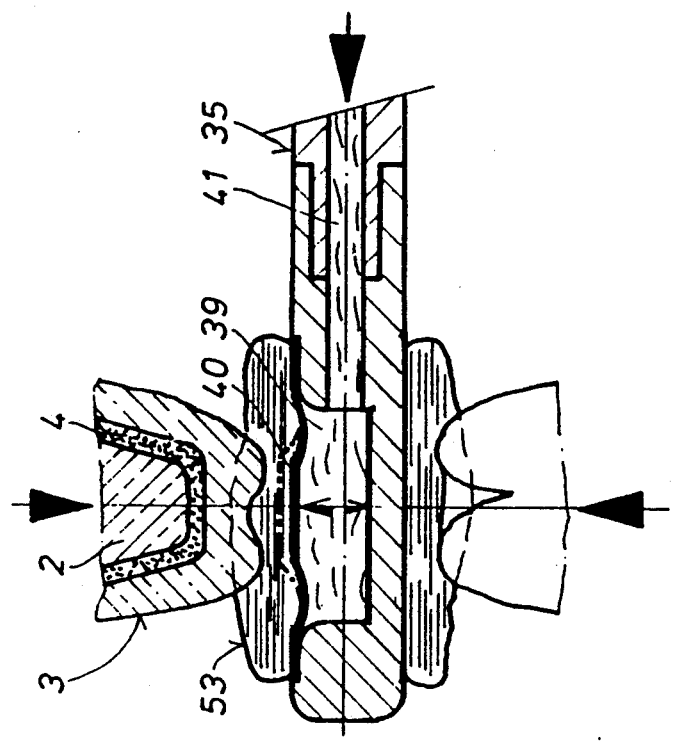
FIG. 3 shows a first embodiment of the resonator according to FIG. 2 in an enlarged representation.
Figure 4:
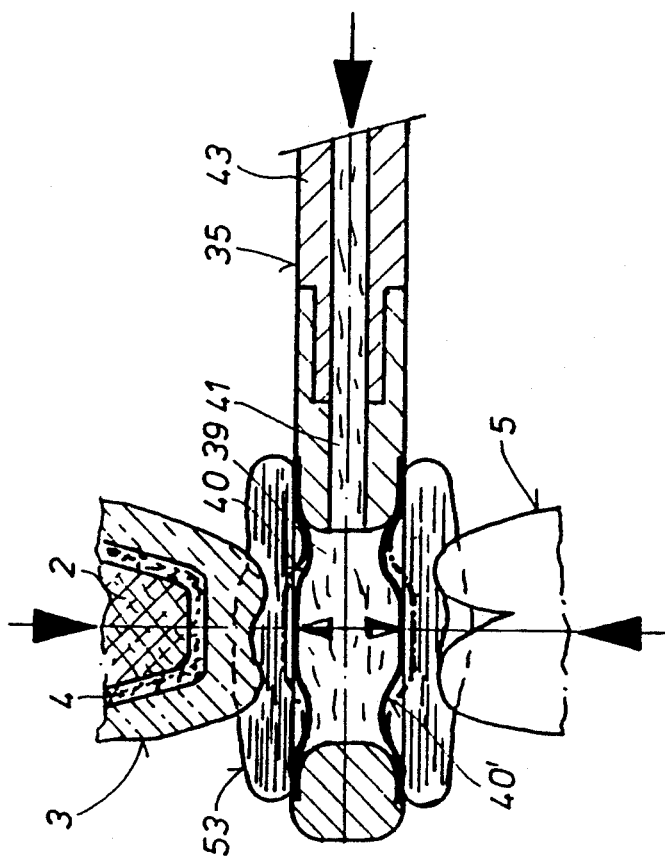
FIG. 4 shows a further embodiment of the resonator of FIG. 2 in an enlarged view.

FIG. 1 represents the inventive device 1 which is especially suitable in dentistry and which serves to transmit mechanical oscillations in order to, as is shown in FIGS. 2 to 4, evenly distribute a binder 4 present between a crown 3 and a tooth stump 2 in a short period of time. The device 1 comprises essentially an actuator 11 which is connected via an electrical line 12 to an electrical power source. The actuator 11 is connected via a hydraulic linkage 13 to a working device via which the mechanical oscillations generated by the actuator 11 are transmitted to the workpiece, for example, a crown or a bridge. The actuator 11 may be embodied in different ways.

According to FIG. 1, the working device may be in the form of resonators 15 to 15'''' provided with a grip portion 14 and usable for individual crowns (15), double crowns (15'), multiple crowns (15''), in scissor crowns (15'''), or for a complete denture (15''''). However, it is also possible to embody the working device as a filling stamp 17 to 17''' comprising a grip portion 16. The filling stamps may be in the form of a tapered stamp 17, a spherical tip 17', a small spatula tip 17'', or a large spatula tip 17'''.

With the aid of a control device 21, coordinated with the actuator 11 and having a switch 25 connected thereto, the stroke, the frequency, and/or the lifting power of the lifting member of the actuator 11 may be adjusted, indicated schematically with the displays 22, 23 and 24.

The actuator 31 which is represented in detail in FIG. 2 is comprised of a housing 34 in which any commercially available, well known solenoid 32 may be arranged, preferably a reversing lifting solenoid. The core of the solenoid represents the lifting member 33. Instead of the solenoid 32 an ultrasonic oscillator, known per se, may be used which acts on the lifting member 33.

Via a hydraulic linkage 35 the actuator 31 is connected to the grip portion 43 that is provided with a pressure chamber 39 sealed off by a diaphragm 40, according to FIG. 3, or, according to FIG. 4, by two diaphragms 40, 40'. The hydraulic linkage 35 is comprised of a line 36 which is filled with an incompressible medium 41, for example, a medicinal oil. The line 36 is provided with a cylinder 37 at the end which is facing the actuator 31. The cylinder 37 has a piston 38 disposed therein. The other end of the line 36 is sealed off by the diaphragms 40, 40'. The line 36 which is preferably formed of a flexible hose is connected via screw connections 42 and 44 to the cylinder 37, respectively, the grip portion 43. The cylinder 37 is connected to the housing 34 of the actuator 31 by a screw connection 45. Furthermore, the resulting annular gap between the cylinder 37 and the piston 38 is sealed by sealings 47.

The lifting member 33 of the actuator 31 acts via two intermediate pieces 33' and 46 onto the piston 38 whereby, in order to prevent canting, the intermediate piece 33' adjacent to the intermediate piece 46 is semi-spherically formed.

When the solenoid 32, respectively, the ultra-sonic oscillator is excited, the lifting movements of the lifting member 33 are transmitted onto the incompressible medium 41 of the hydraulic linkage 35 so that when the crown 3 as well as the tooth 5 directly, or indirectly via the biting cushion 53, rest at and exert a counter force on the diaphragms 40, 40', mechanical oscillations with a frequency of approximately 40 to 100 Hz are transmitted onto the crown 3. The binder 4 between the crown 3 and the tooth stump 2 is thus distributed in a very short period of time, and a flawless fastening of the crown 3 is ensured after curing off the binder 4.

In the area of the cylinder 37 a compensating device 51 is connected to the hydraulic linkage 35 so that a loss of the incompressible medium 41 due to leakage may be replaced. Furthermore, with the aid of a pressure measuring device 52 the pressure within the line 36 may be measured. Excessive loads on the patients are thus preventable because the actuator 31 may be switched off at a predetermined pressure value.

Figure 5:
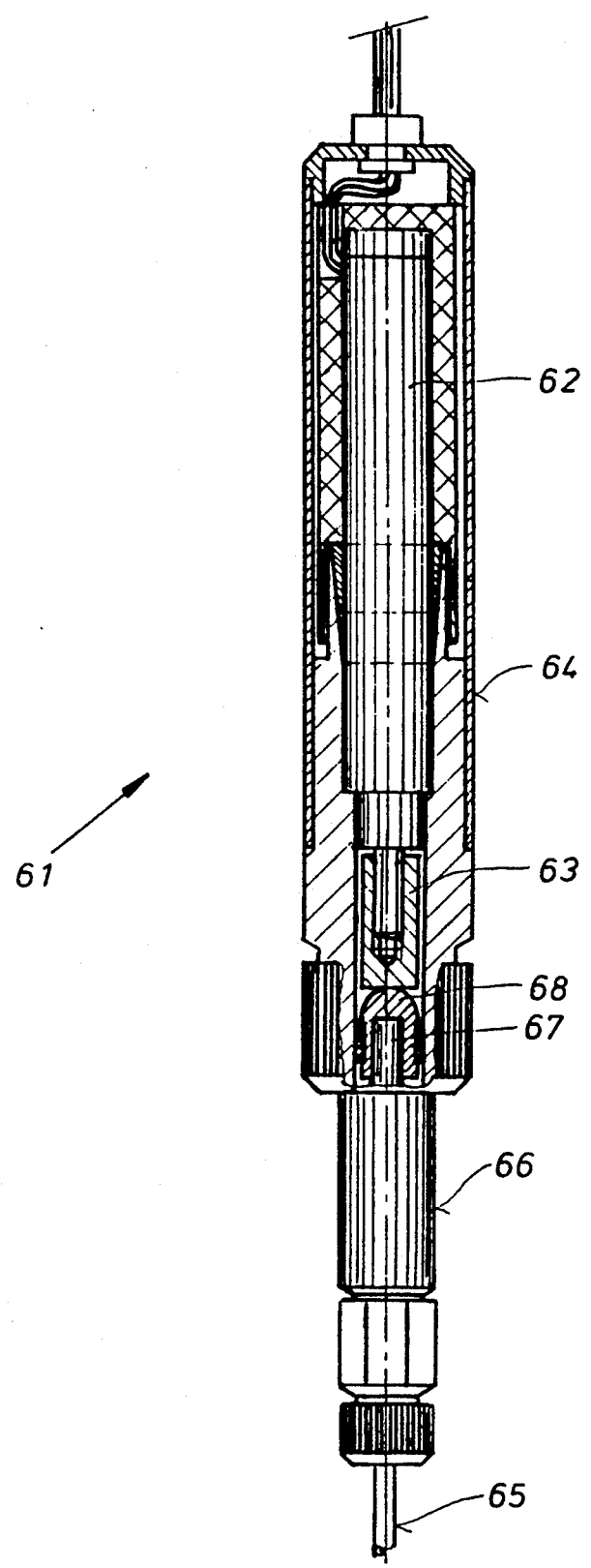
FIG. 5 shows an actuator in the form of a piezoelectric translator.

In the embodiment according to FIG. 5 the actuator 61 is in the form of a piezoelectric translator 62 which is comprised of a plurality of disks in a manner known per se. In order to provide for an axial lifting stroke, the piezoelectric translator 62 is supplied with electrical energy of a corresponding frequency.

The lifting strokes thus generated are transmitted via the lifting member 63 and an adjacently positioned semi-spherical intermediate piece 68 onto the piston 67 which is slidably supported within the cylinder 66. Since the hydraulic linkage 65 is connected to the cylinder 66, the oscillations generated by the piezoelectric translator 62 are transmitted via the hydraulic linkage 65 to the working device.

Figure 6:
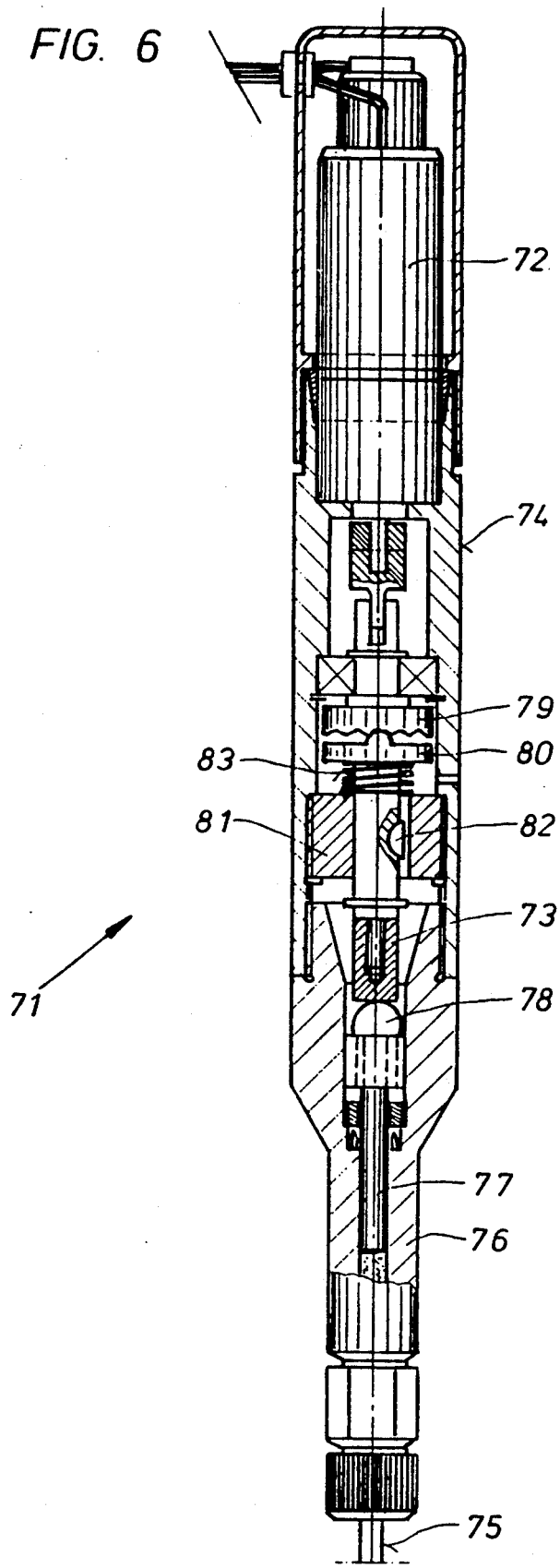
FIG. 6 shows an actuator in the form of a rotation motor.

According to FIG. 6 the actuator 71 is provided with an electric rotation motor 72 for generating oscillations which for transmitting the rotational movement of its drive shaft is provided with a cam disk 79. The cam disk 79 cooperates with the lifting member 73 which is rotationally fixedly connected to a sleeve 81 with a wedge 82, but is axially slidable against the force of a compression spring 83 within the sleeve 81 that is supported at the housing 74. A lifting member 73 at the end face facing the cam disk 79 is provided with a plunger 80 resting at the cam disk 79 so that during a rotation of the cam disk 79 the lifting member 73 is axially displaced. The displacements of the lifting member 73 are transmitted via a semi-spherical intermediate piece 78 onto the piston 77 within the cylinder 76 which acts on the liquid column of the hydraulic linkage 75.

Figure 7:
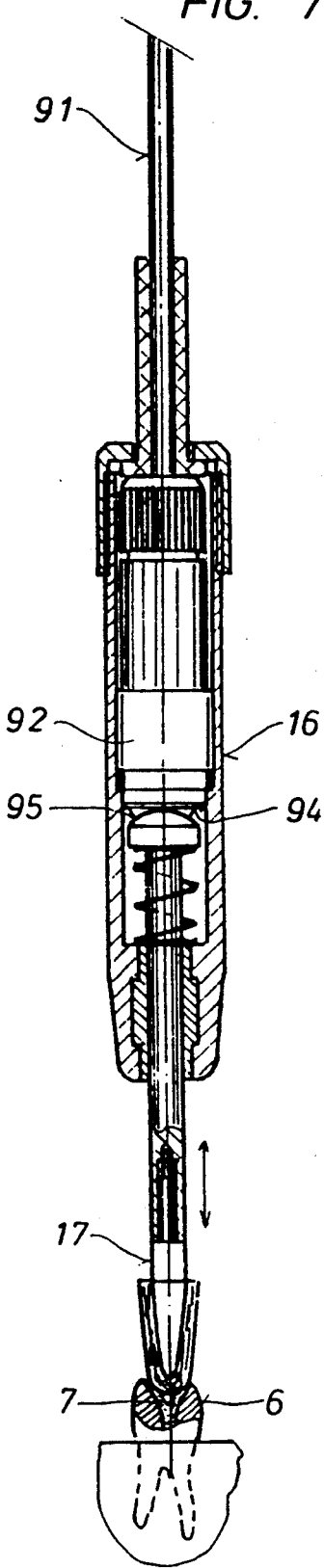
FIG. 7 is a working device in the form of a filling stamp.
Figure 8:
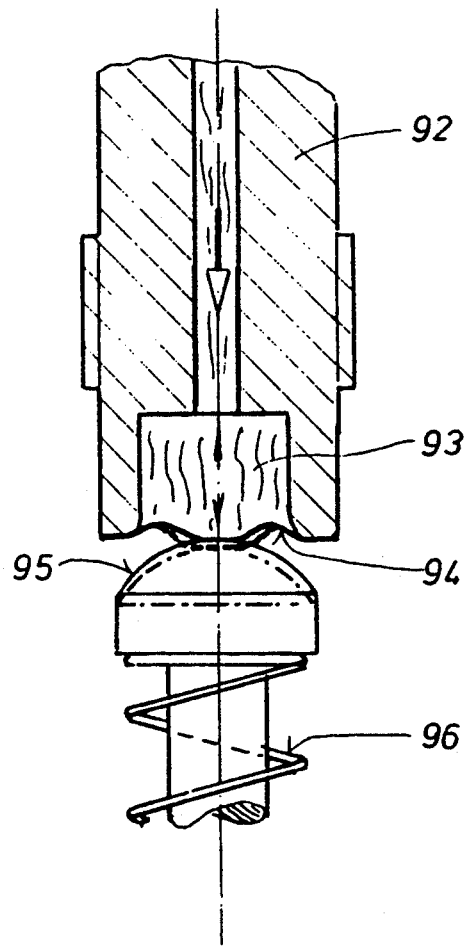
FIG. 8 shows in an enlarged representation a portion of FIG. 7.
Figure 9:
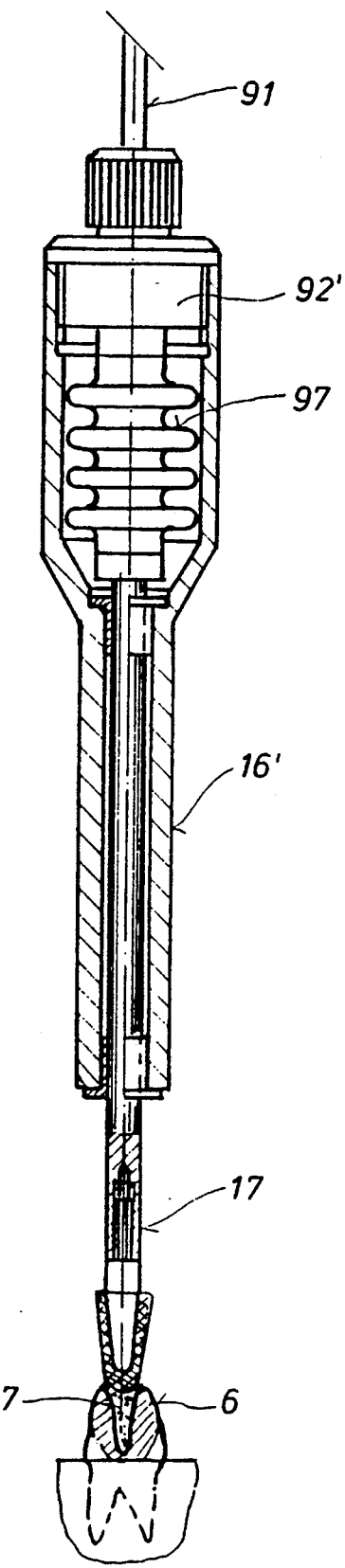
FIG. 9 is a further embodiment of a working device in the form of a filling stamp.

In FIGS. 7 to 9 filling stamps 17 designed to compress by mechanical oscillations fillings 7 introduced into a tooth 6 are represented. The filling stamps 17 are inserted into a respective grip portion 16, 16' and are oscillated by mechanical oscillations of the liquid column of the hydraulic linkage 91.

According to FIGS. 7 and 8 this is achieved by providing a pressure chamber 93 within the housing 92 provided at the end of the hydraulic linkage 91, the pressure chamber being closed off by a membrane 94. A pressure or intermediate piece 95 is pressed onto the diaphragm 94 by the force of the spring 96 so that the oscillations generated by the actuator are transmitted via the diaphragm 94 onto the filling stamp 17.

In the embodiment according to FIG. 9 the housing 92' arranged within the grip portion 16' has a bellows 97 which is axially displaceable by the lifting movements of the actuator transmitted via the liquid column of the hydraulic linkage 91 so that thereby the filling stamp 17 is mechanically oscillated.

The present invention is, of course, in no way restricted to the specific disclosure of the specification and drawings, but also encompasses any modifications within the scope of the appended claims.

What we claim is:

1. A device for generating oscillations for dental applications, comprising:
    an actuator for generating oscillations, said actuator connectable to an energy source and comprising a lifting member;
    a hydraulic linkage with a first and a second end, said first end connected to said lifting member; and
    a working device, connected to said second end of said hydraulic linkage, wherein the oscillations of said actuator are transmitted by said lifting member via said hydraulic linkage to said working device and from said working device to a workpiece.

2. A device according to claim 1, wherein said actuator is a solenoid.

3. A device according to claim 2, wherein said solenoid is a reversing lifting solenoid.

4. A device according to claim 1, wherein said actuator is an ultrasonic oscillator.

5. A device according to claim 1, wherein said actuator is a piezoelectric translator.

6. A device according to claim 1, wherein said actuator is a rotation motor comprising a cam disk and wherein said lifting member is a plunger cooperating with said cam disk.

7. A device according to claim 1, wherein said actuator further comprises a control device for adjusting stroke, frequency, and lifting energy of said lifting member.

8. A device according to claim 1, wherein said hydraulic linkage comprises a line connected between said lifting member and said working device, said line filled with an incompressible medium, and further comprises a cylinder and a piston at said first end, said piston inserted in said cylinder and actuatable by said lifting member.

9. A device according to claim 8, wherein said hydraulic linkage further comprises a diaphragm for closing said line at said second end.

10. A device according to claim 9, wherein said hydraulic linkage further comprises a second semi-spherical intermediate piece interposed between said diaphragm and said working device.

11. A device according to claim 9, wherein said working device is a resonator and wherein said diaphragm is inserted into said resonator.

12. A device according to claim 11, wherein said working device has a grip portion.

13. A device according to claim 9, wherein said diaphragm has connected thereto a pressure-transmitting piece in the form of a parallelepipedal biting cushion made of expanded virgin polytetrafluoroethylene.

14. A device according to claim 8, wherein said hydraulic linkage further comprises a bellows for closing said line at said second end.

15. A device according to claim 8, further comprising a pressure measuring device for measuring a pressure of said incompressible medium in said line.

16. A device according to claim 15, wherein said pressure measuring device is connected to said line in the area of said cylinder.

17. A device according to claim 8, wherein said hydraulic linkage further comprises a first semi-spherical intermediate piece interposed between said piston and said lifting member.

18. A device according to claim 9, wherein said hydraulic linkage further comprises a second semi-spherical intermediate piece interposed between said diaphragm and said working device.

19. A device according to claim 1, wherein said working device is a filling stamp having a grip portion.

20. A device according to claim 1, wherein said working device is a resonator having a grip portion.

21. A device according to claim 8, wherein said line is at least partially comprised of a flexible hose and further comprises a first screw connection for connecting said hose to said cylinder.

22. A device according to claim 21, wherein said line further comprises a second screw connection for connecting said hose to said working device.

23. A device according to claim 22, wherein said line further comprises an intermediate piece and a third screw connection for connecting said hose to said intermediate piece.

24. A device according to claim 8, further comprising a compensating device for compensating a loss of said incompressible medium.

25. A device according to claim 24, wherein said compensating device is connected to said line in the area of said cylinder.

* * * * *